(12) United States Patent
Dankwardt

US007105467B2

(10) Patent No.: US 7,105,467 B2
(45) Date of Patent: Sep. 12, 2006

(54) NICKEL CATALYZED CROSS-COUPLING REACTIONS BETWEEN ORGANOMAGNESIUM COMPOUNDS AND ANISOLE DERIVATIVES

(75) Inventor: John W. Dankwardt, Greenville, NC (US)

(73) Assignee: Pharmacore, Inc., High Point, NC (US)

(*) Notice: Subject to any disclaimer, the term of this patent is extended or adjusted under 35 U.S.C. 154(b) by 180 days.

(21) Appl. No.: 10/615,810

(22) Filed: Jul. 8, 2003

(65) Prior Publication Data

US 2005/0010073 A1  Jan. 13, 2005

(51) Int. Cl.
*B01J 31/00* (2006.01)
*B01J 37/00* (2006.01)
*C08F 4/02* (2006.01)
*C08F 4/60* (2006.01)
*C07C 15/67* (2006.01)

(52) U.S. Cl. .................. 502/103; 502/150; 502/115; 502/117; 502/121; 585/469; 585/454; 106/439

(58) Field of Classification Search ............. 502/150, 502/103, 115, 117, 121; 106/439; 585/469, 585/454
See application file for complete search history.

(56) References Cited

U.S. PATENT DOCUMENTS

| | | | |
|---|---|---|---|
| 3,959,220 A * | 5/1976 | Hechenbleikner et al. .. 524/118 |
| 4,012,399 A * | 3/1977 | Hechenbleikner et al. .... 556/13 |
| 4,263,466 A | 4/1981 | Colon et al. |
| 4,412,856 A | 11/1983 | Brunner et al. |
| 4,508,560 A | 4/1985 | Brunner et al. |
| 4,620,025 A | 10/1986 | Sletzinger et al. |
| 4,724,260 A | 2/1988 | Kirchhoff et al. |
| 4,730,032 A | 3/1988 | Rossi et al. |
| 4,912,276 A | 3/1990 | Puckette |
| 4,916,227 A | 4/1990 | Puckette |
| 4,990,647 A | 2/1991 | Himmler et al. |
| 5,084,204 A | 1/1992 | Reiffenrath et al. |
| 5,128,355 A | 7/1992 | Carini et al. |
| 5,130,439 A | 7/1992 | Lo et al. |
| 5,202,349 A | 4/1993 | Zimmer et al. |
| 5,237,116 A | 8/1993 | Corley |
| 5,264,456 A | 11/1993 | Chandrratna et al. |
| 5,288,895 A | 2/1994 | Bouisett et al. |
| 5,364,943 A | 11/1994 | Rosen et al. |
| 5,365,007 A * | 11/1994 | Wu ............................. 585/528 |
| 5,462,954 A * | 10/1995 | Baker et al. ................. 514/381 |
| 5,532,374 A * | 7/1996 | Lee et al. ..................... 546/167 |
| 5,559,144 A | 9/1996 | Brooks et al. |
| 5,559,277 A | 9/1996 | Beller et al. |
| 5,693,728 A * | 12/1997 | Okamoto et al. ............ 526/115 |
| 5,693,843 A * | 12/1997 | Breikss et al. ............... 558/338 |
| 5,789,634 A * | 8/1998 | Sullivan et al. ............. 570/183 |
| 5,811,549 A * | 9/1998 | Adams et al. ............... 544/123 |
| 5,858,907 A * | 1/1999 | Wang et al. ................. 502/213 |
| 5,874,606 A * | 2/1999 | Huang et al. ................ 558/411 |
| 5,922,898 A | 7/1999 | Miller et al. |
| 6,075,171 A * | 6/2000 | Sullivan et al. .............. 570/129 |
| 6,194,599 B1 | 2/2001 | Miller et al. |
| 6,218,537 B1 * | 4/2001 | Adams et al. ............... 544/122 |
| 6,252,001 B1 | 6/2001 | Babb et al. |
| 6,329,526 B1 * | 12/2001 | Adams et al. ............ 546/274.1 |
| 6,500,849 B1 | 12/2002 | Tegeler et al. |
| 6,562,989 B1 * | 5/2003 | Hartwig et al. ............... 556/21 |
| 6,566,372 B1 | 5/2003 | Zhi et al. |
| 6,569,871 B1 * | 5/2003 | Adams et al. ............... 514/314 |
| 6,590,100 B1 * | 7/2003 | Galland et al. ................ 546/13 |
| 6,759,408 B1 * | 7/2004 | Grubb et al. ............. 514/230.5 |
| 6,962,999 B1 * | 11/2005 | Miller ......................... 546/286 |
| 2003/0100760 A1 | 5/2003 | Miller |
| 2005/0124808 A1* | 6/2005 | Miller ......................... 544/224 |
| 2005/0137402 A1 | 6/2005 | Miller et al. |

FOREIGN PATENT DOCUMENTS

| EP | 0 131 968 | 1/1985 |
|---|---|---|
| EP | 0 470 794 | 2/1992 |
| EP | 0 470 795 | 2/1992 |

OTHER PUBLICATIONS

Pridgen, Lendon, "Oxazolines. 3. Regioselective Synthesis of 2-(Monosubstituted phenyl) and/or Unsymmetrically 2-(Disubstituted phenyl) 2-Oxazolines by Cross-Coupling Grignard Reagents to (Haloaryl)-2-oxazolines", J. Org. Chem., 1982, 47, 4319-4323.*

Pridgen and Killmer, "New Synthesis of 2-Substituted 2-Oxazolines: Transition-Metal-Catalyzed Cross-Coupling of Grignards with 2-(methylthio)-4,4-dimethyl-2-oxazoline", J. Org. Chem., 1981, 46, 5402-5404.*

Organic Syntheses, Coll. vol. 6, p. 407 (1988); vol. 58, p. 127 (1978). "Phosphine-Nickel Complex Catalyzed Cross-Coupling of Grignard Reagents with Aryl and Alkenyl Halides: 1,2-dibutylbenzene".*

Terao, et al. J. Am. Chem. Soc. 2002, 124, 4222-4223, "Nickel-Catalyzed Cross-Coupling Reaction of Grignard Reagents with Alkyl Halides and Tosylates: Remarkable Effect of 1,3-Butadienes".*

(Continued)

*Primary Examiner*—J. A. Lorengo
*Assistant Examiner*—Jennine Brown
(74) *Attorney, Agent, or Firm*—Samuel B. Rollins

(57) ABSTRACT

The present invention provides nickel catalysts and solvents which are useful in a cross-coupling reaction between an organomagnesium compound and an aromatic ether compound, such as an anisole derivative.

18 Claims, No Drawings

OTHER PUBLICATIONS

Ali et al., "Palladium-Catalysed Cross-Coupling Reactions of Arylboronic Acids with .PI.-Deficient Heteroaryl Chlorides", Tetrahedron, vol. 48, pp. 8117-8126, (1992).

Beletskaya, et al., "The nickel-catalyzed Sonogashira-Hagihara reaction", Tetrahedron Letters, vol. 44, pp. 5011-5013, (2003).

Bleicher and Cosford, "Aryl- and Heteroaryl-alkyne coupling reactions catalyzed by palladium on carbon and CuII in an aqueous medium," SYNLETT, 11:1115-1116, (1995).

Bringmann et al., "The Directed Synthesis of Biaryl Compounds: Modern Concepts and Strategies", Angew. Chem, Int. Ed. Engl., vol. 29, 977-991, (1990).

Carini et al., "Nonpeptide Angiotensin II Receptor Antagonists: The Discovery of a Series of N-(Bipheynylymethyl)imidazoles as Potent, Orally Active Antihypertensives", J. Med, Chem., vol. 34, pp. 2525-2547, (1991).

Cibulka et al., "Metal Ion Chelates of Lipoophilic Alkyl Diazinyl Ketoximes as Hydrolytic Catalysts", Collect. Czech. Chem. Commun., vol. 64, pp. 1159-1179, (1999).

Clough et al., "Coupling of Nonequivalent Aromatic Rings by Soluble Nickel Catalysts. A Genereal Route to the 1,8-Diarylnaphthalenes.sub. 1a", J. Org. Chem., vol. 41, pp. 2252-2255, (1976).

Colon et al., "Coupling of Aryl Chlorides by Nickel and Reducing Metals", J. Org. Chem., vol. 51, pp. 2627-2637 (1986).

Diek et al., "Palladium Catalyzed Synthesis of Aryl, Heterocyclic and Vinylic Acetylene Derivatives", Organometallic Chem., 93:529 (1975).

Fuson, R.C. and W.S. Friedlander, "Displacement of substituents in phenyl 2,4,6,-triisoplylphenyl ketone by the action of Grignard reagents", J. Am. Chem. Soc., vol. 75, pp. 5410-5411, (1953).

Fuson, R.C. et al., "The reaction of Grignard reagents with the cyanobenzoyldurenes;", J. Org. Chem., vol. 16, pp. 648-654, (1951).

Grushin et al., "Transformations of Chloroarenes, Catalyzed by Transition-Metal Complexes", Chem. Rev., vol. 94, pp. 1047-1062, (1994).

House et al., "Reactions of the 1,8-Dipenylanthracene System", J. Org. Chem., vol. 45, pp. 1807-1817 (1980).

House et al., "Unsummetrically Substituted 1, 8-Diarlanthracenes", J. Org. Chem., vol. 51, pp. 921-929, (1986).

Kageyama et al., "Nickel-Catalyzed Cross-Coupling Reaction of Aryl Halides in Pyridine. A Practical Synthesis of 4-Methylbiphenyl-2-carbonitrile As a Key Intermediate of Angiotensine II Receptor Antagonists", Synlett, pp. 371-372, (1994).

Kalinin et al., "Carbon—Carbon Bond Formation in Heterocycles Using Ni- and Pd-Catalyzed Reactions", Synthesis, pp. 413-432, (1992).

Mantlo et al., "Potent, Orally Active Imidazo 4,5-b pyridine-Based Angiotensin II Receptor Antagonists", J. Med. Chem., vol. 34, pp. 2919-2922 (1991).

Miller and Farrell, "Synthesis of functionally substitutedunsymmetriczal Biaryls via a novel double metal catalyzed coupling reaction", Tetrahedron Letters, vol. 39, pp. 7275-7278 (1998).

Miller and Farrell, "Synthesis of functionally substitutedunsymmetriczal Biaryl via novel double metal catalyzed coupling reaction", Tetrahedron Letters, vol. 39, pp. 7275-7278 (1998).

Miller et al., "Nickel Catalyzed Cross-Coupling and Animation Reactions of Aryl Nitriles", Synthesis, No. 11, pp. 1643-1648, (2003).

Miller et al., "Nickel catalyzed cross-coupling of modified alkyl and alkenyl Grignard reagents with aryl- and Heteroaryl nitriles: activation of the C-CN bond", Tetrahedron Letters, vol. 44, pp. 1907-1910, (2003).

Miller, "C—C Bond Activation with selective functionalization: preparation of unsymmetrical Biaryls for benzonitriles", Tetrahedron Letters, vol. 42. pp. 6991-6993, (2001).

Milner, D.J. et al., "The mono-alkyldecyanation of tetrafluoroterephtalonitrile by reaction with Gringard reagents," J. Organometallic Chem., vol. 302, pp. 147-152, (1986).

Miyaura et al, "The Palladium-Catalyzed Cross-Coupling Reaction of Phenylboronic Acid with Haloarenes in the Presence of Bases", Synthetic Communications, vol. 11, p. 513 (1981).

Nakao, et al., "Nickel-Catalyzed Arylcyanation of Alkynes", Journal American Chemical Society, (2004).

Negishi et al., "Selective Carbon—Carbon Bond Formation via Transition Metal Catalysis. 3. A Highly Selective Synthesis of Unsymmetrical Biaryls and Diarylmethanes by the Nickel- or Palladium-Catalyzed Reaction of Aryl- and Benzylzine Derivatives with Aryl Halides", J. Org. Chem., vol. 42, pp. 1821-1823 (1977).

Penney et al., "Alkynylation of benxonitriles via nickel catalyzed C—C bond activation", vol. 45, pp. 4989-4992, (2004).

Percec et al., "Aryl Mesylates in Metal Catalyzed Homo- and Cross-Coupling Reactions. 4. Scope and Limitations of Aryl Mesylates in Nickel Catalyzed Cross-Coupling Reactions", J. Org. Chem., vol. 60, 6895-6903, (1995).

Rossi et al., "Palladium-Catalyzed Syntheses of Naturally-Occurring acetylenic Thiophens and Related Compounds", Tetrahedron, vol. 40, pp. 2773-2779, (1984).

Saito et al., "A Synthesis of Biaryls via Nickel (O)-Catalyzed Cross-Coupling Reaction of Chloroarenes with Phenylboronic Acids", Tetrahedron Letters, vol. 37, pp. 2993-2996, (1996).

Sanisbury, "Modern Methods of Aryl—Aryl Bond Formation", Tetrahedron, vol. 36, pp. 3327 to 3359, (1980).

Silbille et al., "Electrochemical Conversion of Functionalised Aryl Chlorides and Bromides to Arylzinc Species", J. Chem. Soc. Chem. Comm., pp. 283-284 (1992).

Sonogashira, et al., "Development of Pd-Cu catalyzed cross-coupling of terminal acetylenes with $sp^2$-carbon halides", Journal of Organo Metallic Chem., vol. 653, pp. 46-49, (2002).

Stanforth, S.P., "Catalytic cross-coupling reactions in Biaryl synthesis," Tetrahedron, vol. 54, pp. 263-303 (1998).

Tamao et al., "Nickel-Phosphine Complex-Catalyzed Grignard Coupling. I. Cross-Coupling of Alkyl, Aryl, and Alkenyl Grignard Reagents with Aryl and Alkenyl Halides: General Scope and Limitations", Bull. Chem. Soc. Japan, vol. 49, pp. 1958-1969, (1976).

Voegtle et al., "Tweezer-shaped hydrocarbons", Chemical Abstracts, vol. 125, pp. 219-235 (1992).

Wenkert, et al., "Transformation of Carbon-Oxygen into Carbon—Carbon Bonds Mediated by Low-Valent Nickel Species", Journal of Organic Chemistry, vol. 49, pp. 4894-4899, (1984).

Wenkert, et al., "Nickel-Induced Conversion of Carbon-Oxygen into Carbon—Carbon Bonds, One-Step Transformations of Enol Ethers into Olefins and Aryl Ethers into Biaryls", vol. 101, pp. 2246-2247, (1979).

Whitall et al. "Organometallic Complexes for Nonlinear Optics. 3.1 Molecular Quadratic Hyperpolarizabilities of Ene-, Imine-, and Azo-Linked Buthenium, sigma, -Acetylides: Z-ray Crystal Structure of Ru (E) -4, 4' -C. tplbond.CC6H4Ch: CHC6H4N02: (PPh3) 2 (.eta. -C5H5)", Organometallics, 15(7), pp. 1935-1941, (1996).

Zembayashi et al., "Nickel-Phosphine Complex-Catalyzed Homo Coupling of Aryl Halides in the Presence of Zinc Powder", Tetrahedron Letters No. 47, pp. 4089-4092 (1977).

Zhu et al., "The Direct Formation of Functionalized Alkyl(aryl)zinc Halides by Oxidative Addition of Highly Reactive Zinc with Organic Halides and Their Reactions with Acid Chlorides, alpha beta.-Unsaturated Ketones, and Allylic, Aryl, and Vinyl Halides", J. Org. Chem., vol. 56, pp. 1445-1453 (1991).

* cited by examiner

US 7,105,467 B2

NICKEL CATALYZED CROSS-COUPLING REACTIONS BETWEEN ORGANOMAGNESIUM COMPOUNDS AND ANISOLE DERIVATIVES

FIELD OF THE INVENTION

The present invention relates to a cross-coupling reaction between an organometallic compound and an aromatic ether compound using a nickel catalyst.

BACKGROUND OF THE INVENTION

Formation of a carbon-carbon bond remains one of the most important reactions in organic chemistry and has applications in a variety of fields including medicinal chemistry, agricultural chemistry, polymer chemistry and material science. While many carbon-carbon bond forming reactions involve an electrophile (e.g., carbonyl compound) and a nucleophile (e.g., organometallic compound), others require the presence of a coupling catalyst.

One particularly useful nickel catalyzed reaction involves coupling an organometallic compound (e.g., Grignard reagent) with enol ethers or aryl ethers. See Wenkert et al., *J. Amer. Chem. Soc.*, 1979, 101, 2246 and Wenkert et al., *J. Org. Chem.*, 1984, 49, 4894. Wenkert et al. report using bis(triphenylphosphine)nickel dichloride or [1,3-bis(diphenylphosphino)propane]nickel dichloride catalyst in an aromatic solvent such as toluene and benzene. However, there are many limitations to these reactions. For example, although the reaction between a methoxy substituted naphthalene compound and phenylmagnesium halide is relatively efficient, a coupling reaction between a methoxy substituted phenyl compound (e.g., anisole derivative) is significantly lower. Furthermore, aryl ethers are "inert to [substitution by] methylmagnesium bromide." See Wenkert et al., *J. Amer. Chem. Soc.*, 1979, 101, 2246 at 2247.

Moreover, some aromatic solvents such as benzene are highly carcinogenic. Thus, the use of these solvents increases the cost of the overall process due to disposal and safe handling requirements. In addition, in some instances it is difficult to remove all traces of these highly carcinogenic solvents. Hence, the use of these solvents in the preparation of products that are directly utilized or consumed by humans (e.g., therapeutics) is discouraged or prohibited.

There remains a need for a catalyst that is effective and more efficient in forming a carbon-carbon bond between a non-activated aromatic ether, including heteroaryl ether, and an alkyl or aryl organometallic compound. There is also a need for a catalyst that does not require the use of an aromatic solvent in a coupling reaction.

SUMMARY OF THE INVENTION

The present invention provides a method for forming a carbon-carbon bond between an organometallic compound and an aromatic ether compound using a nickel catalyst to produce a coupled aryl compound. The nickel catalyst of the present invention comprises a phosphino-ligand which has no more than one aromatic group attached directly to the phosphorous atom.

In one aspect of the present invention, the phosphino-ligand is of the formula —$PR^3R^4R^5$, wherein each of $R^3$ and $R^4$ is independently a saturated hydrocarbon moiety having from one to about twelve carbon atoms; and $R^5$ is selected from the group consisting of a saturated hydrocarbon moiety having from one to about twelve carbon atoms and an aryl moiety having from six to fourteen carbon ring atoms.

Aromatic ethers which are useful in methods of the present invention include those having the formula $Ar^1$—$OR^2$, wherein $Ar^1$ is aryl such as naphthyl, phenanthracenyl or phenyl; and $R^2$ is selected from alkyl, heteroalkyl, cycloalkyl, aryl, aralkyl and —$SiR^9R^{10}R^{11}$, where each of $R^9$, $R^{10}$ and $R^{11}$ is independently a hydrocarbon moiety.

Another aspect of the present invention provides a process for producing substituted aryl compounds using a nickel catalyzed cross-coupling reaction between organometallic compounds and aromatic ether compounds under non-aromatic solvent conditions.

DETAILED DESCRIPTION OF THE INVENTION

Definitions

"Alkyl" refers to a saturated linear or branched monovalent hydrocarbon moiety having one to twelve, preferably one to eight, more preferably one to six, and still more preferably one to four, carbon atoms. Exemplary alkyl groups include methyl, ethyl, propyl, iso-propyl, butyl, tert-butyl, iso-butyl, pentyl, hexyl, octyl, and the like.

"Alkylene" refers to a saturated linear or branched divalent hydrocarbon moiety having one to twelve, preferably one to eight, more preferably one to six, and still more preferably one to four, carbon atoms. Exemplary alkylene groups include methylene, ethylene, propylene, iso-propylene, butylene, tert-butylene, iso-butylene, pentylene, hexylene, octylene, and the like.

"Alkenyl" refers to a linear or branched monovalent hydrocarbon moiety comprising at least one carbon-carbon double bond having two to twelve carbon atoms. With the understanding that the point of attachment of an alkenyl group is through one of the carbon atom in the carbon-carbon double bond. Alkenyl groups can optionally be substituted with one or more substituents, such as aryl, cycloalkyl, heteroaryl, halo, haloalkyl and heteroalkyl. Exemplary alkenyl groups include ethenyl, propenyl, 2-propenyl, butenyl, 2-butenyl, pentenyl, hexenyl, octenyl, and the like.

"Alkynyl" refers to a linear or branched monovalent hydrocarbon moiety comprising at least one carbon-carbon triple bond having two to twelve carbon atoms. With the understanding that the point of attachment of an alkynyl group is through one of the carbon atom in the carbon-carbon triple bond. Alkynyl groups can optionally be substituted with one or more substituents, such as aryl, cycloalkyl, heteroaryl, halo, haloalkyl and heteroalkyl. Exemplary alkynyl groups include ethynyl, propynyl, butynyl, pentynyl, hexynyl, octynyl, and the like.

The term "alkoxide" refers to a moiety of the formula —$OR^a$, wherein $R^a$ is $C_1$–$C_{20}$ hydrocarbon as defined herein. Preferably $R^a$ is $C_1$–$C_{12}$ alkyl, $C_6$–$C_{10}$ aryl, $C_3$–$C_8$ cycloalkyl, $C_7$–$C_{12}$ aralkyl or $C_4$–$C_{10}$ cycloalkylalkyl.

"Aryl" refers to a monovalent mono-, bi- or tricyclic aromatic hydrocarbon moieties of six to fourteen carbon ring atoms. Exemplary aryl groups include phenyl, naphthyl and anthracenyl. The aryl group can optionally be substituted with one or more substituents. Typical substituents for aryl groups include alkyl, haloalkyl, heteroalkyl, alkoxy, halo, cycloalkyl, heteroaryl and another aryl group. Exemplary aryl groups include phenyl, 1-naphthyl, and 2-naphthyl, anthracenyl, and the like.

"Aralkyl" refers to a moiety of the formula —$R^bR^c$ wherein $R^b$ is an alkylene group and $R^c$ is an aryl group as defined above, e.g., benzyl and phenylethyl.

"Carboxylate" refers to a moiety of the formula —OC(=O)$R_d$, wherein $R_d$ is hydrogen or a hydrocarbon moiety.

"Cycloalkyl" refers to a saturated monovalent mono-, bi- or tri-cyclic hydrocarbon moiety of three to twelve, preferably three to ten and more preferably three to eight, ring carbons.

"Cycloalkylalkyl" refers to a moiety of the formula —$R^e$—$R^f$, wherein $R^f$ is cycloalkyl and $R^e$ is alkylene as defined herein.

"Grignard reagent," which is well known to one skilled in the art, refers to any compound that comprises a —MgX moiety (wherein X is halide) that is attached to a carbon atom.

The terms "halo" and "halide" are used interchangeably herein and refer to fluoro, bromo, chloro or iodo.

"Haloalkyl" means an alkyl group, as defined above, that is substituted with one or more same or different halides. Exemplary haloalkyl groups include —$CH_2Cl$, —$CF_3$, —$CH_2CF_3$, —$CH_2CCl_3$, etc., as well as those alkyl groups in which all alkyl hydrogen atoms are replaced by fluorine atoms, i.e., perfluoroalkyl.

"Heteroalkyl" refers to an alkyl group containing one or more heteroatoms (i.e., N, O or S) or heteroatom-containing substituents. Exemplary heteroalkyl groups include 2-methoxyethyl, 2-N,N-dimethylethyl, and the like.

"Heteroaryl" refers to a monovalent mono-, bi- or tricyclic aromatic moiety of five to sixteen ring atoms containing one or more, preferably one, two or three, ring heteroatoms each independently selected from the group consisting of N, O and S, the remaining ring atoms being C. The heteroaryl ring can optionally be substituted with one or more substituents provided above in the definition of the aryl group. Exemplary heteroaryl groups include, pyridyl, furanyl (i.e., furyl), thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, and the like.

"Hydrocarbon" refers to any moiety that comprises hydrogen and carbon. A hydrocarbon compound can be saturated, unsaturated (including aromatic), cyclic, non-cyclic or a combination of such structures. Exemplary hydrocarbon moieties include, but are not limited to, alkyl, alkenyl, cycloalkyl, aryl, aralkyl, cycloalkylalkyl, and the like.

"Halogenated hydrocarbon" refers to a hydrocarbon moiety in which one or more hydrogen has been replaced with halide. Halogenated hydrocarbon included perhalogenated hydrocarbon moiety in which all of the hydrogen has been replaced with halides.

"Saturated hydrocarbon moiety" refers to a hydrocarbon moiety that has no carbon-carbon double or triple bond. Exemplary saturated hydrocarbon moieties include alkyl and cycloalkyl groups.

"Sulfonate" refers to a moiety of the formula —OS(O)$_2$$R^e$, wherein $R^e$ is hydrocarbon or halogenated hydrocarbon.

The terms "as defined herein", "as defined above", "those defined above" and "those defined herein" when referring to a variable incorporates by reference the broad definition of the variable as well as preferred, more preferred and most preferred definitions, if any.

The terms "treating", "contacting" and "reacting" means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Throughout this disclosure, combinations of preferred variables described herein form other preferred embodiments. In this manner, a wide range of preferred embodiments are contemplated to be within the scope of this invention.

DESCRIPTION OF THE EMBODIMENTS

General

A nickel catalyzed coupling reaction between aryl ethers and organomagnesium compounds has been known for many years; however, its use has not been widely accepted due to its limited scope of applicability. For example, while naphthyl ethers produce a relatively high yield of coupled products, the yield of coupled products for phenyl ethers is significantly lower. In addition, alkyl Grignard reagents are reported to not undergo a coupling reaction with aryl ethers. See Wenkert et al. *J. Amer. Chem. Soc.*, 1979, 101, 2246 and *J. Org. Chem.*, 1984, 49, 4894. Moreover, currently most nickel catalyzed coupling reactions between aryl ethers and organomagnesium compounds use an aromatic solvent, such as benzene and toluene, some of which are known to be highly carcinogenic.

Surprisingly and unexpectedly, the present inventors have discovered that certain nickel compounds catalyze a cross-coupling reaction between aromatic ethers and organomagnesium compounds that were previously reported to be inert or relatively unreactive to such reaction conditions. Thus, methods of the present invention allow access to a wide variety of substituted aryl compounds that were previously inaccessible using a nickel-catalyzed coupling reaction between an aromatic ether and an organomagnesium compound. Without being bound by any theory, it is believed that increased catalytic activity of nickel compounds of the present invention is due to inter alia the presence of one or more phosphino-ligands having a relatively large steric hindrance and/or better σ-donor capability than convention phosphino-ligands which have two or more aromatic hydrocarbon moieties directly attached to the phosphorous atom, e.g., triphenylphosphine.

Moreover, it has also been discovered by the present inventors that some non-aromatic solvents afford a much higher yield of desired coupling products.

I. Method of Coupling

One aspect of the present invention provides a method for coupling an organomagnesium compound of the formula: $R^1$—$MgX^1$ with an aromatic ether compound of the formula: $Ar^1$—$OR^2$ to produce a coupled aromatic compound of the formula: $Ar^1$—$R^1$, wherein $R^1$ is selected from aryl and heteroaryl; $R^2$ is selected from alkyl, heteroalkyl, cycloalkyl, aryl, aralkyl and a moiety of the formula —$SiR^9R^{10}R^{11}$, wherein each of $R^9$, $R^{10}$ and $R^{11}$ is independently a hydrocarbon moiety; $Ar^1$ is aryl or heteroaryl; and $X^1$ is a magnesium metal ligand, which is discussed in detail under the section entitled Organomagnesium Compounds.

The method generally comprises admixing the organomagnesium compound with the aromatic ether compound in the presence of a nickel catalyst which has one or more phosphino-ligands of the formula —$PR^3R^4R^5$, wherein each of $R^3$ and $R^4$ is independently a saturated hydrocarbon moiety having from one to about twelve carbon atoms; and $R^5$ is selected from a saturated hydrocarbon moiety having from one to about twelve carbon atoms and an aryl moiety having from six to fourteen carbon ring atoms.

Organomagnesium Compounds

Unlike conventional nickel catalyzed cross-coupling processes, a wide variety of organomagnesium compounds are useful in methods of the present invention, including aryl and heteroaryl magnesium compounds. The organomagnesium compounds are typically represented by Formula I:

   I wherein $R^1$ is those defined herein and $X^1$ is a magnesium ligand.

The organomagnesium compound can be preformed prior to being added to the reaction mixture or it can be generated in situ, e.g., via a metal-halogen exchange reaction or a transmetallation reaction.

In one embodiment of preferred organomagnesium compounds, $R^1$ is aryl. Especially preferred organomagnesium compounds are those where $R^1$ is an optionally substituted phenyl group.

Preferably, the magnesium ligand $X^1$ is selected from halide (such as chloride, bromide or iodide), sulfonate (e.g., mesylate, tosylate or triflate), alkoxide, and the like. Previously, only aryl Grignard reagents (e.g., phenylmagnesium halide) have been reported to undergo a nickel-catalyzed cross-coupling reaction with aryl ethers. In contrast, nickel catalysts of the present invention provide an efficient cross-coupling reaction between aromatic ethers and a wide variety of organomagnesium compounds, including aryl, heteroaryl, alkyl, alkenyl, alkynyl and cycloalkyl Grignard reagents.

Aromatic Ethers

Currently, aryl ethers, which are known to undergo a nickel-catalyzed cross-coupling reaction with aryl Grignard reagents, are generally limited to naphthyl ethers. While some phenyl ether derivatives do undergo a cross-coupling reaction with a phenyl Grignard reagent, the yield of the corresponding cross-coupled products are significantly lower compared to the corresponding naphthyl ether derivatives. Furthermore, it has been reported that anisole derivatives (i.e., phenyl group comprising a methyl ether substituent) do not undergo a nickel catalyzed cross-coupling reaction with alkyl Grignard reagents. See Wenkert et al.

In contrast, a wide range of aromatic ethers, including heteroaryl ethers, are useful in methods of the present invention, including naphthyl ethers, phenyl ethers (such as anisole and its derivatives), phenanthracenyl ethers, and heteroaryl ethers (such as pyridinyl ethers, furyl ethers, thiophenyl ethers, pyrimidinyl ethers, and the like). Thus, methods of the present invention provide access to a wide variety of compounds that were previously inaccessible using a nickel catalyzed cross-coupling reaction.

In one embodiment, useful aromatic ethers are represented by Formula (II):

   II wherein $R^2$ is selected from alkyl, heteroalkyl, cycloalkyl, aryl, aralkyl and a moiety of the formula —$SiR^9R^{10}R^{11}$, wherein each of $R^9$, $R^{10}$ and $R^{11}$ is independently a hydrocarbon moiety; and $Ar^1$ is aryl or heteroaryl. As stated in the Definitions section, aryl and heteroaryl groups can optionally be substituted with one or more substituents. When substituents are present in the aryl or heteroaryl moiety, the substituents are preferably relatively inert to the reaction conditions.

Preferred aryl groups of $Ar^1$ include, but are not limited to, naphthyl, phenanthacenyl, phenyl, and the like, each being optionally substituted. Within this aryl groups, optionally substituted phenyl is particularly useful in methods of the present invention. Especially preferred aryl groups of $Ar^1$ are anisole derivatives. Anisole is well known to one skilled in the art as referring to a phenyl group that is substituted with a methoxy group. Thus, the term "anisole derivative" refers to an anisole compound that has one or more additional substituents on the phenyl groups. Preferably, the additional substituents that are present in anisole derivatives are relatively inert to the nickel-catalyzed cross-coupling reactions disclosed herein, with the exception that the additional substituents may comprise a protecting group that may be removed under the reaction conditions. In fact, the term "derivative" is used herein to generally refer to a compound that has one or more additional substituents in addition to the parent structure. The additional substituents preferably being relatively inert to the reaction conditions, with the exception that the additional substituents may comprise a protecting group that may be removed under the reaction conditions.

Preferred heteroaryl groups of $Ar^1$ include, but are not limited to, pyridinyl, furyl, thiophenyl, and the like, each being optionally substituted.

In one embodiment, the aromatic ether is a silyl ether, i.e., compound of Formula II where $R^2$ is —$SiR^9R^{10}R^{11}$. In this embodiment, preferably each of $R^9$, $R^{10}$ and $R^{11}$ is independently $C_1$–$C_{12}$ hydrocarbon. Particularly preferred $C_1$–$C_{12}$ hydrocarbons of $R^9$, $R^{10}$ and $R^{11}$ are $C_1$–$C_{12}$ alkyl, $C_3$–$C_8$ cycloalkyl, $C_6$–$C_{10}$ aryl or $C_7$–$C_{12}$ aralkyl.

One group of preferred aromatic ethers of Formula II are those in which $R^2$ is alkyl or heteroalkyl. Within this group of preferred aromatic ethers, those where $R^2$ is alkyl are particularly preferred, with methyl and ethyl being especially preferred alkyl groups.

Thus, unlike conventional nickel catalyzed cross-coupling reactions, methods of the present invention are useful in forming a variety of coupled products, including substituted aromatic compounds resulting from a cross-coupling reaction between aromatic ethers (including heteroaryl ethers) and a wide variety of organomagnesium compounds, such as aryl and heteroaryl organomagnesium compounds.

Nickel Catalyst

Typically, nickel catalysts that are added to the coupling-reaction mixture in methods of the present invention include one or more, preferably two, phosphino-ligands. Moreover, each phosphino-ligand has at most one aromatic group directly attached to the phosphorous atom. Preferably, the phosphino-ligand has no aromatic group that is attached directly to the phosphorous atom.

It should be appreciated that while the nickel catalysts added to the reaction mixture are described as having one or more phosphino-ligands, in the course of the reaction, it is possible, and often likely, that one or more phosphino-ligands may become dissociated or displaced from the nickel metal. Thus, when describing the nickel catalysts, the present disclosure refers to the form of nickel catalysts that is believed to be generated in situ or one that is added to the reaction mixture, and not necessarily the actual active species that promotes or catalyzes the cross-coupling reaction described herein.

In one embodiment, the phosphino-ligand is of the formula:

$$PR^3R^4R^5 \qquad \text{III}$$

wherein each of $R^3$ and $R^4$ is independently a saturated hydrocarbon moiety having from one to about twelve carbon atoms; and $R^5$ is selected from a saturated hydrocarbon moiety having from one to about twelve carbon atoms and an aryl moiety having from six to fourteen carbon ring atoms. Exemplary $R^5$ aryl moities include, but are not limited to, phenyl, naphthyl, ferrocene, and the like, each of which can be optionally substituted.

In one embodiment, the saturated hydrocarbon moiety is selected from $C_1$–$C_{12}$ alkyl and $C_3$–$C_{10}$ cycloalkyl. Within this group of saturated hydrocarbon moieties, $C_1$–$C_6$ alkyl and $C_3$–$C_8$ cycloalkyl groups are particularly preferred.

One group of preferred phosphino-ligands are those wherein $R^3$ and $R^4$ are saturated hydrocarbon moieties each independently selected from $C_1$–$C_{12}$ alkyl and $C_3$–$C_{10}$ cycloalkyl. Within this group, phosphino-ligands wherein $R^3$ and $R^4$ are independently $C_1$–$C_6$ alkyl and $C_3$–$C_8$ cycloalkyl are particularly preferred. Further preferred are phosphino-ligands wherein each of $R^3$ and $R^4$ is independently selected from isopropyl, methyl, tert-butyl, iso-butyl, neopentyl and cyclohexyl. Especially preferred within this group of phosphino-ligands are those wherein each of $R^3$ and $R^4$ is independently neopentyl or cyclohexyl.

In another group of preferred phosphino-ligands, $R^5$ is optionally substituted phenyl or a saturated hydrocarbon moiety selected from $C_1$–$C_{12}$ alkyl and $C_3$–$C_{10}$ cycloalkyl. Among optionally substituted phenyl groups for $R^5$, unsubstituted phenyl is particularly preferred. As for the saturated hydrocarbon moiety for $R^5$, $C_1$–$C_6$ alkyl and $C_3$–$C_8$ cycloalkyl are particularly preferred. Especially useful $R^5$ groups are isopropyl, methyl, tert-butyl, iso-butyl, neopentyl, cyclohexyl and phenyl, with neopentyl, cyclohexyl and phenyl being particularly preferred.

Still further, combinations of the preferred groups described herein form other preferred embodiments. For example, one particularly preferred group of phosphino-ligand is selected from triisopropylphosphine, dicyclohexylphenylphosphine, di-tert-butylmethylphosphine, tri-isobutylphosphine, tri-neopentylphosphine and tricyclohexylphosphine. In this manner, a variety of preferred phosphino-ligands are embodied within the present invention.

Alternatively, the phosphino-ligand is a bidentate phosphino-ligand of the formula:

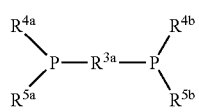

i.e., $(R^{4a})(R^{5a})P$—$R^{3a}$—$P(R^{4b})(R^{5b})$, wherein $R^{3a}$ is alkylene, each of $R^{4a}$ and $R^{4b}$ is independently a saturated hydrocarbon moiety having from one to about twelve carbon atoms, and each of $R^{5a}$ and $R^{5b}$ is independently selected from a saturated hydrocarbon moiety having from one to about twelve carbon atoms and an aryl moiety having from six to fourteen carbon ring atoms. Preferably, the saturated hydrocarbon moiety is selected from $C_1$–$C_{12}$ alkyl and $C_3$–$C_{10}$ cycloalkyl. Within this group of saturated hydrocarbon moieties, $C_1$–$C_6$ alkyl and $C_3$–$C_8$ cycloalkyl groups are particularly preferred.

One group of particular preferred bidentate phosphino-ligands of the present invention are those wherein $R^{3a}$ is $C_2$–$C_6$ alkylene. Within this group of bidentate phosphino-ligands, preferably $R^{3a}$ is selected from the group ethylene, propylene and butylene.

In another group of preferred bidentate phosphino-ligands, each of $R^{4a}$ and $R^{4b}$ is independently a saturated hydrocarbon moiety selected from $C_1$–$C_{12}$ alkyl and $C_3$–$C_{10}$ cycloalkyl. Within this group of bidentate phosphino-ligands, those in which each of $R^{4a}$ and $R^{4b}$ is independently selected from $C_1$–$C_6$ alkyl and $C_3$–$C_8$ cycloalkyl are particularly preferred. Further preferred within this group of bidentate phosphino-ligands are those wherein each of $R^{4a}$ and $R^{4b}$ is independently selected from isopropyl, methyl, tert-butyl, iso-butyl, neopentyl and cyclohexyl. Especially preferred among this group of bidentate phosphino-ligands are those in which each of $R^{4a}$ and $R^{4b}$ is independently neopentyl or cyclohexyl.

Yet in another group of preferred bidentate phosphino-ligands, each of $R^{5a}$ and $R^{5b}$ is independently selected from optionally substituted phenyl and a saturated hydrocarbon moiety selected from $C_1$–$C_{12}$ alkyl and $C_3$–$C_{10}$ cycloalkyl. Within optionally substituted phenyl groups, unsubstituted phenyl is particularly preferred. As for the saturated hydrocarbon moiety for $R^{5a}$ and $R^{5b}$, $C_1$–$C_6$ alkyl and $C_3$–$C_8$ cycloalkyl are particularly preferred. Especially useful within this group of bidentate phosphino-ligands are those in which each $R^{5a}$ and $R^{5b}$ is independently selected from isopropyl, methyl, tert-butyl, iso-butyl, neopentyl, cyclohexyl and phenyl, with neopentyl, cyclohexyl and phenyl being particularly useful.

Still further, combinations of preferred groups for the bidentate phosphino-ligands described above form other preferred embodiments. For example, one particularly preferred group of bidentate phosphino-ligands is selected from bis(dicyclohexylphosphino)ethane, bis(dicyclohexylphosphino)propane, bis(dicyclohexylphosphino)butane, and the like. In this manner, a variety of preferred bidentate phosphino-ligands are also embodied within the present invention.

As stated above, nickel catalysts of the present invention include at least one phosphino-ligand. In one particular aspect of the present invention, the nickel catalysts comprise phosphino-ligands of formula III or IIIA or a combination thereof. The nickel catalyst can also comprise one or more anionic ligand(s).

In one particular embodiment of the present invention, the nickel catalysts of the present invention are of the formula:

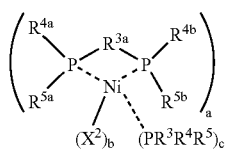

wherein $R^{3a}$ is alkylene; each of $R^3$, $R^4$, $R^{4a}$ and $R^{4b}$ is independently a saturated hydrocarbon moiety having from one to about twelve carbon atoms; each of $R^5$, $R^{5a}$ and $R^{5b}$ is selected from a saturated hydrocarbon moiety having from one to about twelve carbon atoms and an aryl moiety having from six to fourteen carbon ring atoms; and each of variables a, b and c is independently an integer from 0 to 4, provided the sum of a+b+c is 4 or less, preferably 2 or 4. Preferred groups for $R^{3a}$, $R^3$, $R^4$, $R^{4a}$, $R^{4b}$, $R^5$, $R^{5a}$ and $R^{5b}$ are same as those described above in reference to the phosphino-ligands of Formulas III and IIIA.

The subscripts in Formula IV represent the number of each ligands that may be present on the nickel catalyst. Thus, each of the subscripts a and b is independently an integer from 0 to 2; the subscript c is an integer from 0 to 4, provided that the total number of ligand coordination on the nickel metal is no more than four. For example, when a is 2, the nickel metal is tetra-coordinated, and therefore b and c are 0. Similarly, when c is 4, a and b are 0. Other combinations of ligands are also possible, such as a=0, b=2, c=2; a=1, b=2, c=0; and a=1, b=0, c=2.

The variable $X^2$ in Formula IV is a co-ligand with each co-ligand being independently selected. Suitable co-ligands are well known to one skilled in the art and include halides, carboxylates (such as acetate, propionate, butynoate and the like), sulfonates (including triflates), 1,3-diketones (e.g., acetylacetone and dibenzoylmethane, and the like).

In one embodiment, each co-ligand (i.e., $X^2$) is independently selected from halide and carboxylate. Preferably, each co-ligand is independently selected from halide and acetate. A particularly preferred co-ligand is halide with chloride being an especially preferred co-ligand.

The nickel catalyst can be preformed before being added to a reaction mixture or it can be formed in situ, for example, by contacting a phosphine compound of Formula III or IIIA with a nickel salt, such as $Ni(X^2)_2$, wherein $X^2$ is a co-ligand defined above.

As used herein, the term "phosphine compound" refers to a phosphine compound that is not coordinated to the nickel metal. Thus, the term "phosphine compound" is used to distinguish from "phosphino-ligand" which refers to a phosphine compound which is coordinated to the nickel metal. It should be appreciated that when a phosphine compound is admixed with a nickel compound, the phosphine compound may become coordinated to the nickel metal, thereby becoming a phosphino-ligand. Thus, the terms "phosphine compound" and "phosphino-ligand" are used simply to characterize the phosphine species that is being added to the reaction mixture, i.e., a phosphine compound refers to a phosphine species that is not coordinate to any metal at the time it is added to the reaction mixture, whereas phosphino-ligand refers to a phosphine species that is coordinated to a metal at the time it is added to the reaction mixture.

In one particular embodiment of the present invention, the nickel catalyst is of the formula:

  V wherein each $X^2$ is independently a co-ligand; $R^6$ is cycloalkyl; and each of $R^7$ and $R^8$ is independently selected from the group consisting of a saturated hydrocarbon moiety having from one to about twelve carbon atoms and an aryl moiety having from six to fourteen carbon atoms.

One group of preferred nickel catalysts are those in which each of $R^7$ and $R^8$ is independently a saturated hydrocarbon moiety having from one to about twelve carbon atoms with $C_1$–$C_{12}$ alkyl and $C_3$–$C_{10}$ cycloalkyl groups being a particularly preferred saturated hydrocarbon moieties. Especially preferred nickel catalysts include compound of Formula V wherein each of $R^7$ and $R^8$ is independently $C_3$–$C_{10}$ cycloalkyl. A particularly preferred cycloalkyl group is cyclohexyl.

Preferred co-ligands of the nickel catalysts of Formula V include halide, carboxylate, sulfonate, and 1,3-diketone. Within this group of co-ligands, halide is a particularly preferred co-ligand with chloride being especially preferred co-ligand.

Alternatively, the reactive nickel catalysts can be formed in situ by adding an appropriate nickel salt, such as $NiCl_2$, $NiBr_2$, $NiI_2$, Ni(acac), and the like, and a suitable amount of the phosphine compound described herein.

Reaction Conditions

Reaction conditions for methods of the present invention generally involve admixing an organomagnesium compound, which can be preformed or generated in situ, and an aromatic ether compound in the presence of a nickel catalyst. A variety of factors influence the reaction rate and/or the yield of a cross-coupled product, including the reaction solvent, catalytic activity of the nickel catalyst, reactivity of the aromatic ether and organometallic compounds, the concentration of each reagents and the reaction temperature.

The amount of nickel catalyst used in methods of the present invention can vary significantly depending on a variety of factors, including the turn-over number of the catalyst (i.e., the average number of coupled-product produced by each nickel catalyst molecule) and other factors that are mentioned above. Generally, however, the amount of nickel catalyst used in methods of the present invention ranges from about 0.1 mole %, to about 10 mole %, with 1 mole % to about 5 mole % being a typical amount of nickel catalyst used. However, is should be appreciated that the amount of nickel catalyst used in methods of the present invention is not limited to these specific ranges.

While not necessary, it has been found that addition of at least about 1 equivalent, preferably at least about 2 equivalents, of a phosphine compound of formula $PR^3R^4R^5$ (wherein $R^3$, $R^4$ and $R^5$ are those defined above) relative to the amount of nickel catalyst added to the reaction mixture often results in a higher yield and/or a faster coupling-rate.

The coupling reaction can generally be conducted at a range of temperatures, typically from room temperature to the boiling point of the reaction solvent used. Suitable reaction temperature depends on a variety of factors including, but not limited to, the substrate (i.e., starting material), the phosphino ligand and the nickel catalyst, and the solvent. Typically, however, the coupling reaction of the present invention is conducted at a temperature of from about 20° C. to about 110° C. Often the reaction temperature is at least about 60° C. As an illustrative example, a preferred reaction temperature range in methods of the present invention is from about 60° C. to about 80° C. when tAmOME is used as a solvent along with a nickel catalyst comprising tricyclohexylphosphine ligand. However, it should be appreciated that a suitable reaction temperature range is not limited to those disclosed herein.

The reaction time can range from a few hours to a few days depending on a variety of factors, including the reactivity and concentrations of each reagents, the amount of catalyst used, the reaction temperature and the type of solvent used, as well as other factors known to one skilled in the art. In general, however, the reaction time ranges from about 1 hour to about 24 hours. Typically, the reaction time ranges from about 5 hours to about 20 hours, and more typically from about 10 hours to about 15 hours.

Alternatively, the cross-coupling reactions of the present invention can be carried out using a microwave reactor and irradiating the reaction mixture with microwave radiation. In this manner, the reaction time can be significantly reduced to few minutes rather than few hours.

In this aspect of the invention, a variety of solvents are useful, including aromatic (e.g., benzene, toluene and xylenes) and non-aromatic solvents. However, surprising and unexpectedly, the present inventors have found certain non-aromatic solvents provides higher yield of the desired coupled product. In particular, non-aromatic solvents that are useful in methods of the present invention include ethers, such as tetrahydrofuran (THF), tetrahydropyran (THP), dibutyl ether, t-amyl methyl ether (t-AmOMe), diisopropyl ether, t-butyl methyl ether (MTBE), diethyl ether, 1,2-dimethoxyethane (DME) and dioxanes, e.g., 1,4-dioxane and 1,3-dioxolane; acetals or ketals such as diethoxymethane (DEM) and dimethoxymethane (DMM); and amines such as dicyclohexyl methyl amine.

In one particular embodiment, the reaction solvent is selected from toluene, THF, THP, dibutyl ether, t-AmOMe, diisopropyl ether, t-butyl methyl ether, diethyl ether, DME, dioxanes, DEM, DMM, dicyclohexyl methyl amine, and a combination of two or more solvents thereof. Preferably, the reaction solvent is selected from THF, DME, 1,4-dioxane, THP, MTBE, diethyl ether, dicyclohexyl methyl amine, t-AmOMe, diisopropyl ether, DEM, di-n-butyl ether, and a combination of two or more solvents thereof. More preferably, the reaction solvent is selected from MTBE, diethyl ether, dicyclohexyl methyl amine, t-AmOMe, diisopropyl ether, DEM, di-n-butyl ether, and a combination of two or more solvents thereof. Especially preferred reaction solvent is selected from t-AmOMe, diisopropyl ether, DEM, di-n-butyl ether, and a combination of two or more solvents thereof.

It should be appreciated that reaction conditions employed in methods of the present invention are not limited to those specific ranges and examples given herein.

II. Process for Producing Substituted Aryl Compounds

Another aspect of the present invention provides a process for producing a substituted aryl compound of the formula: $Ar^1$—$R^1$, wherein $R^1$ is selected from aryl and heteroaryl; and $Ar^1$ is aryl. The process involves admixing an organometallic compound of the formula: $(R^1)_n$-M and an aromatic ether compound of the formula: $Ar^1$—$OR^2$ in a non-aromatic solvent in the presence of a nickel catalyst comprising a phosphino-ligand, wherein $Ar^1$ and $R^1$ are as defined above, $R^2$ is selected from alkyl, heteroalkyl, cycloalkyl, aryl and aralkyl; M is a metal or a metal halide salt; and the subscript n is an integer from 1 to the oxidation state of the metal M.

Useful aromatic ethers, organomagnesium compounds, non-aromatic solvents and reaction conditions are similar to those described above in the section entitled "Method of Coupling." Of the non-aromatic solvents discussed above, dibutyl ether as well as acetals and ketals, such as diethoxymethane (DEM) and dimethoxymethane (DMM), are preferred non-aromatic solvents. Especially useful non-aromatic solvents are diethoxymethane and dibutyl ether.

A wide varied of nickel catalysts are useful in this aspect of the present invention, including those described above. In addition, conventional nickel catalysts, such as those having two or more aryl moieties directly attached to the phosphorous atom of the phosphino-ligand, e.g., triphenylphosphine, are also useful in this aspect of the present invention.

III. Catalyst Composition

Another aspect of the present invention provides a catalyst composition comprising one equivalent of the nickel catalyst of Formula IV above and at least one, preferably at least two, equivalents of the phosphine compound of Formula III. Alternatively, the phosphine compound can be the bidentate phosphine compound of Formula IIIA. It should be appreciated that because of its bidentate nature or capability, when the catalyst composition comprises the bidentate phosphine compound of Formula IIIA, the amount of phosphine compound IIIA that is present in the catalyst composition is typically about one-half the amount of the phosphine compound of Formula III that is needed.

While not necessary, typically the phosphine compound that is present in the catalyst composition is same as the phosphino-ligand that is present in the nickel catalyst. Thus, when the nickel catalyst that is present in the catalyst composition is of Formula V above, the phosphine compound that is present in this composition is of the formula:

$$PR^6R^7R^8 \qquad \qquad VI$$

wherein $R^6$ is cycloalkyl; and each of $R^7$ and $R^8$ is selected from a saturated hydrocarbon moiety having from one to about twelve carbon atoms and an aryl moiety having from six to fourteen carbon ring atoms.

EXAMPLES

The following examples are offered to illustrate, but not to limit the claimed invention.

Example 1

Preparation of 6-(4-methylphenyl)-1,2,3,4-tetrahydronaphthalene by nickel catalyzed coupling of 6-methoxy-1,2,3,4-tetrahydronaphthalene with p-tolylmagnesium bromide.

A THF solution of p-tolylmagnesium bromide (20.0 mL, 20.0 mmol) was placed under vacuum to remove the volatiles. The solvent was replaced with diethoxymethane (20.0 mL). In a separate flask, NiCl$_2$(PCy$_3$)$_2$  (where Cy=cyclohexyl) (355 mg, 0.514 mmol), PCy$_3$ (285 mg, 1.018 mmol), and 6-methoxy-1,2,3,4-tetrahydronaphthalene (1.639 g, 10.11 mmol) was combined in diethoxymethane (2.5 mL). The Grignard reagent was added to this mixture under a nitrogen atmosphere. The resulting solution was stirred 2 minutes at room temperature and then warmed to 90° C. for 15 hours. The reaction was quenched with half saturated aqueous ammonium chloride solution (30 mL) and was extracted with MTBE (3×30 mL). The combined organic layer was dried over MgSO$_4$, filtered and concentrated. The residue was purified by silica gel chromatography (eluted with heptane) to provide 6-(4-methylphenyl)-1,2,3,4-tetrahydronaphthalene (1.43 g, 64% yield)

In a separate experiment using the conditions described above with the exception that tridecane was added as an internal standard, 6-(4-methylphenyl)-1,2,3,4-tetrahydronaphthalene was produced in 95% GC yield.

Comparative Example 1a

Preparation of 6-(4-methylphenyl)-1,2,3,4-tetrahydronaphthalene by nickel catalyzed coupling of 6-methoxy-1,2,3,4-tetrahydronaphthalene with p-tolylmagnesium bromide using an in situ generated nickel catalyst in THF.

In a flask was combined Ni(acac)$_2$ (24.8 mg, 0.0965 mmol), PCy$_3$ (54.0 mg, 0.193 mmol), tridecane (242 mg, 1.315 mmol, as an internal standard), and 6-methoxy-1,2,3, 4-tetrahydronaphthalene (321 mg, 1.979 mmol). The Grignard reagent (1 M in THF, 5.90 mmol) was added to this mixture under a nitrogen atmosphere. The resulting solution was stirred 2 minutes at room temperature and then warmed to 60° C. for 15 hours. A sample was withdrawn and quenched with an aqueous sodium citrate solution (1 M). The aqueous solution was extracted with ethyl acetate. GC analysis of the organic phase showed the presence of 6-(4-methylphenyl)-1,2,3,4-tetrahydronaphthalene (1.162 mmol, 59% yield), 4-methylphenol (0.227 mmol), bitoluene (0.530 mmol), and 6-methoxy-1,2,3,4-tetrahydronaphthalene (0.677 mmol) in the reaction mixture.

Comparative Example 1b

Preparation of 6-(4-methylphenyl)-1,2,3,4-tetrahydronaphthalene by nickel catalyzed coupling of 6-methoxy-1,2,3,4-tetrahydronaphthalene with p-tolylmagnesium bromide using $NiCl_2(PCy_3)_2$ in THF.

In a reaction flask was placed $NiCl_2(PCy_3)_2$ (51.0 mg, 0.0739 mmol), tridecane (251 mg, 1.364 mmol, as an internal standard), and 6-methoxy-1,2,3,4-tetrahydronaphthalene (264 mg, 1.627 mmol). The Grignard reagent (1 M in THF, 4.10 mmol) was added to this mixture under a nitrogen atmosphere at room temperature. The resulting solution was warmed to 60° C. for 15 hours. A sample was withdrawn and quenched with an aqueous sodium citrate solution (1 M). The aqueous solution was extracted with ethyl acetate. GC analysis of the organic phase showed the presence of 6-(4-methylphenyl)-1,2,3,4-tetrahydronaphthalene (0.993 mmol, 61% yield), bitoluene (0.52 mmol), and 6-methoxy-1,2,3,4-tetrahydronaphthalene (0.471 mmol) in the reaction mixture.

Comparative Example 1c

Preparation of 6-(4-methylphenyl)-1,2,3,4-tetrahydronaphthalene by nickel catalyzed coupling of 6-methoxy-1,2,3,4-tetrahydronaphthalene with p-tolylmagnesium bromide using $NiCl_2(PCy_3)_2$/2 $PCy_3$ in THF.

In a reaction flask was placed $NiCl_2(PCy_3)_2$ (61.2 mg, 0.0886 mmol), $PCy_3$ (49.0 mg, 0.175 mmol), tridecane (255 mg, 1.386 mmol, as an internal standard), and 6-methoxy-1,2,3,4-tetrahydronaphthalene (273 mg, 1.683 mmol). The Grignard reagent (1 M in THF, 5.0 mmol) was added to this mixture under a nitrogen atmosphere at room temperature. The resulting solution was warmed to 60° C. for 15 hours. A sample was withdrawn and quenched with an aqueous sodium citrate solution (1 M). The aqueous solution was extracted with ethyl acetate. GC analysis of the organic phase showed the presence of 6-(4-methylphenyl)-1,2,3,4-tetrahydronaphthalene (1.272 mmol, 76% yield), bitoluene (0.50 mmol), and 6-methoxy-1,2,3,4-tetrahydronaphthalene (0.357 mmol) in the reaction mixture.

Comparative Example 1d

Preparation of 6-(4-methylphenyl)-1,2,3,4-tetrahydronaphthalene by nickel catalyzed coupling of 6-methoxy-1,2,3,4-tetrahydronaphthalene with p-tolylmagnesium bromide using $NiCl_2(PPh_3)_2$ in toluene.

The Grignard reagent (1 M in ether, 5.0 mmol) was placed under vacuum to remove all volatiles. Toluene (5.0 mL) was then added to the Grignard reagent. In a separate reaction flask was placed $NiCl_2(PPh_3)_2$ (62.0 mg, 0.0948 mmol), tridecane (282 mg, 1.532 mmol, as an internal standard), and 6-methoxy-1,2,3,4-tetrahydronaphthalene (334 mg, 2.059 mmol). The Grignard reagent in toluene was then transferred to this mixture under a nitrogen atmosphere at room temperature. The resulting solution was warmed to 110° C. for 15 hours. A sample was withdrawn and quenched with an aqueous sodium citrate solution (1 M). The aqueous solution was extracted with ethyl acetate. GC analysis of the organic phase showed the presence of 6-(4-methylphenyl)-1,2,3,4-tetrahydronaphthalene (0.598 mmol, 29% yield), bitoluene (0.419 mmol), and 6-methoxy-1,2,3,4-tetrahydronaphthalene (1.043 mmol) in the reaction mixture.

Comparative Example 1e

Screening of other solvents in the preparation of 6-(4-methylphenyl)-1,2,3,4-tetrahydronaphthalene by $NiCl_2$ $(PCy_3)_2$ mediated coupling of 6-methoxy-1,2,3,4-tetrahydronaphthalene with p-tolylmagnesium bromide.

The procedure was identical to Example 1, with the exception that no additional $PCy_3$ was added and the solvent was varied as outlined in the table.

| Solvent | Reaction Time | % Yield (MeO-tetrahydronaphthalene) | % Yield (Me-phenyl-tetrahydronaphthalene) |
|---|---|---|---|
| THF | 15 h | 78 | 11 |
| toluene | 15 h | 9 | 76 |
| i-Pr$_2$O | 15 h | 0 | 93 |
| (Et$_2$O)$_2$CH$_2$ | 6 h | 10 | 82 |
| t-AmOMe | 6 h | 8 | 65 |
| n-Bu$_2$O | 6 h | 0 | 87 |

Comparative Example 1f

Screening of other nickel catalysts with variation of the phosphine ligand in the preparation of 6-(4-methylphenyl)-1,2,3,4-tetrahydronaphthalene by nickel catalyzed coupling of 6-methoxy-1,2,3,4-tetrahydronaphthalene with p-tolylmagnesium bromide in i-Pr$_2$O.

The procedure was identical to Example 1, with the exception that the nickel catalyst was generated from the dichloronickel (II) phosphine catalyst. No additional phoshine ligand was added.

| Phoshine | Reaction Time | MeO—[tetralin] % Yield | Me—C6H4—[tetralin] % Yield |
|---|---|---|---|
| PMe₃ | 3 h | 69 | 14 |
| PMe₃ | 15 h | 33 | 33 |
| PEt₃ | 3 h | 86 | 0 |
| PEt₃ | 15 h | 75 | 7 |
| Pi-Bu₃ | 2.7 h | 57 | 24 |
| Pi-Bu₃ | 15 h | 32 | 42 |
| Pi-Pr₃ | 2.5 h | 20 | 68 |
| Pi-Pr₃ | 15 h | <1 | 82 |
| PCy₃ | 3 h | 0 | 89 |
| PCy₃ | 15 h | 0 | 93 |
| PhPCy₂ | 3 h | 18 | 76 |
| PhPCy₂ | 15 h | <1 | 92 |
| Ph₂PCy | 3 h | 46 | 44 |
| Ph₂PCy | 15 h | 7 | 81 |
| Ph₃P | 3 h | 81 | 8 |
| Ph₃P | 15 h | 74 | 15 |

Comparative Example 2

Preparation of 6-(4-methylphenyl)-1,2,3,4-tetrahydronaphthalene by nickel catalyzed coupling of 6-trimethylsiloxy-1,2,3,4-tetrahydronaphthalene with p-tolylmagnesium bromide using NiCl₂(PCy₃)₂/2 PCy₃ in diethoxymethane.

In a reaction flask was placed NiCl₂(PCy₃)₂ (36.6 mg, 0.0530 mmol), PCy₃ (35.0 mg, 0.125 mmol), tridecane (166.7 mg, 0.904 mmol, as an internal standard), and 6-trimethylsiloxy-1,2,3,4-tetrahydronaphthalene (211.4 mg, 0.957 mmol). The solvent in the Grignard reagent (1 M in ether, 3.0 mmol) was exchanged with t-AmOMe (6.0 mL) and this solution added to the above catalyst mixture under a nitrogen atmosphere at room temperature. The resulting solution was stirred for several minutes at room temperature and then warmed to 60° C. for 15 hours. A sample was withdrawn and quenched with an aqueous sodium citrate solution (1 M). The resulting aqueous solution was extracted with ethyl acetate. GC analysis of the organic phase showed the presence of 6-(4-methylphenyl)-1,2,3,4-tetrahydronaphthalene (0.637 mmol, 67% yield) and bitoluene (0.407 mmol) and p-methylphenol (0.223 mmol) in the reaction mixture.

Comparative Example 3

Preparation of 6-(4-methylphenyl)-1,2,3,4-tetrahydronaphthalene by nickel catalyzed coupling of N,N-dimethyl-N-[2-(5,6,7,8-tetrahydronaphthalen-2-yloxy)ethyl]amine with p-tolylmagnesium bromide using NiCl₂(PCy₃)₂/2 PCy₃ in diethoxymethane.

In a reaction flask was placed NiCl₂(PCy₃)₂ (69.0 mg, 0.0999 mmol), PCy₃ (57.8 mg, 0.206 mmol), tridecane (328 mg, 1.778 mmol, as an internal standard), and N,N-dimethyl-N-[2-(5,6,7,8-tetrahydronaphthalen-2-yloxy)ethyl]amine (409 mg, 1.867 mmol). The solvent in the Grignard reagent (1 M in ether, 6.0 mmol) was exchanged with diethoxymethane (6.0 mL) and this solution added to the above catalyst mixture under a nitrogen atmosphere at room temperature. The resulting solution was stirred for several minutes at room temperature and then warmed to 95° C. for 15 hours. A sample was withdrawn and quenched with an aqueous sodium citrate solution (1 M) and was extracted with ethyl acetate. GC analysis of the organic phase showed the presence of 6-(4-methylphenyl)-1,2,3,4-tetrahydronaphthalene (1.851 mmol, 99% yield) and bitoluene (0.654 mmol) and p-methylphenol (0.575 mmol) in the reaction mixture.

Comparative Example 4

Preparation of 6-(4-methylphenyl)-1,2,3,4-tetrahydronaphthalene by nickel catalyzed coupling of 6-(2-methoxyethoxy)-1,2,3,4-tetrahydronaphthalene with p-tolylmagnesium bromide using NiCl₂(PCy₃)₂/2 PCy₃ in diethoxymethane.

In a reaction flask was placed NiCl₂(PCy₃)₂ (77.7 mg, 0.1125 mmol), PCy₃ (58.6 mg, 0.209 mmol), tridecane (232 mg, 1.261 mmol, as an internal standard), and 6-(2-methoxyethoxy)-1,2,3,4-tetrahydronaphthalene (505 mg, 2.452 mmol). The solvent in the Grignard reagent (1 M in ether, 6.0 mmol) was exchanged with diethoxymethane (5.0 mL) and this solution added to the above catalyst mixture under a nitrogen atmosphere at room temperature. The resulting solution was stirred for several minutes at room temperature and then warmed to 100° C. for 15 hours. A sample was withdrawn and quenched with an aqueous sodium citrate solution (1 M). The resulting aqueous solution was extracted with ethyl acetate. GC analysis of the organic phase showed the presence of 6-(4-methylphenyl)-1,2,3,4-tetrahydronaphthalene (1.881 mmol, 76% yield) and bitoluene (0.521 mmol) and p-methylphenol (0.301 mmol) in the reaction mixture.

Comparative Example 5

Preparation of 6-(4-methylphenyl)-1,2,3,4-tetrahydronaphthalene by nickel catalyzed coupling of 6-methoxy-1,2,3,4-tetrahydronaphthalene with m-tolylmagnesium bromide using NiCl₂(PCy₃)₂/2 PCy₃ in i-Pr₂O/MTBE.

In a reaction flask was placed NiCl₂(PCy₃)₂ (49.0 mg, 0.0710 mmol), PCy₃ (44.0 mg, 0.157 mmol), tridecane (333 mg, 1.806 mmol, as an internal standard), and 6-methoxy-1,2,3,4-tetrahydronaphthalene (222 mg, 1.368 mmol). The solvent in the Grignard reagent (1 M in ether, 3.70 mmol) was exchanged with i-$Pr_2O$ (8.0 mL) and MTBE (2.0 mL) and this solution added to the above catalyst mixture under a nitrogen atmosphere at room temperature. The resulting solution was stirred for several minutes at room temperature and then warmed to 80° C. for 15 hours. A sample was withdrawn and quenched with an aqueous sodium citrate solution (1 M). The resulting aqueous solution was extracted with ethyl acetate. GC analysis of the organic phase showed the presence of 6-(4-methylphenyl)-1,2,3,4-tetrahydronaphthalene (1.030 mmol, 75% yield) and 6-methoxy-1,2,3,4-tetrahydronaphthalene (0.131 mmol) and bitoluene (0.376 mmol) and m-methylphenol (0.220 mmol) in the reaction mixture.

Comparative Example 6

Preparation of 4-methyl-1,1'-biphenyl by nickel catalyzed coupling of phenetole with p-tolylmagnesium bromide using $NiCl_2(PCy_3)_2$/2 $PCy_3$ in n-$Bu_2O$.

In a reaction flask was placed $NiCl_2(PCy_3)_2$ (59.1 mg, 0.0856 mmol), $PCy_3$ (50.7 mg, 0.1811 mmol), tridecane (423 mg, 2.299 mmol, as an internal standard), and phenetole (210 mg, 1.721 mmol). The solvent in the Grignard reagent (1 M in ether, 5.0 mmol) was exchanged with n-$Bu_2O$ (5.0 mL) and this solution added to the above catalyst mixture under a nitrogen atmosphere at room temperature. The resulting solution was stirred for several minutes at room temperature and then warmed to 125° C. for 2 hours. A sample was withdrawn and quenched with an aqueous sodium citrate solution (1 M). The resulting aqueous solution was extracted with ethyl acetate. GC analysis of the organic phase showed the presence of 4-methyl-1,1'-biphenyl (1.210 mmol, 70% yield) and phenetole (0.239 mmol) in the reaction mixture.

Comparative Example 7

Preparation of 4-methyl-1,1'-biphenyl by nickel catalyzed coupling of (trifluoromethoxy)benzene with p-tolylmagnesium bromide using $NiCl_2(PCy_3)_2$/2 $PCy_3$ in diethoxymethane.

In a reaction flask was placed $NiCl_2(PCy_3)_2$ (81.1 mg, 0.1175 mmol), $PCy_3$ (71.6 mg, 0.2557 mmol), tridecane (242 mg, 1.312 mmol, as an internal standard), and (trifluoromethoxy)benzene (360 mg, 2.222 mmol). The solvent in the Grignard reagent (1 M in ether, 7.0 mmol) was exchanged with diethoxymethane (8.0 mL) and this solution added to the above catalyst mixture under a nitrogen atmosphere at room temperature. The resulting solution was stirred for several minutes at room temperature and then warmed to 90° C. for 15 hours. A sample was withdrawn and quenched with an aqueous sodium citrate solution (1 M). The resulting aqueous solution was extracted with ethyl acetate. GC analysis of the organic phase showed the presence of 4-methyl-1,1'-biphenyl (0.513 mmol, 23% yield) and (trifluoromethoxy)benzene (1.351 mmol) and bitoluene (0.732 mmol) in the reaction mixture.

Comparative Example 8

Preparation of 4-methyl-1,1'-biphenyl by nickel catalyzed coupling of phenyltrimethylsilyl ether with p-tolylmagnesium bromide using $NiCl_2(PCy_3)_2$/2 $PCy_3$ in diethoxymethane.

In a reaction flask was placed $NiCl_2(PCy_3)_2$ (81.6 mg, 0.1182 mmol), $PCy_3$ (66.4 mg, 0.237 mmol), tridecane (328 mg, 1.783 mmol, as an internal standard), and phenyltrimethylsilyl ether (370 mg, 2.225 mmol). The solvent in the Grignard reagent (1 M in ether, 7.0 mmol) was exchanged with diethoxymethane (8.0 mL) and this solution added to the above catalyst mixture under a nitrogen atmosphere at room temperature. The resulting solution was stirred for several minutes at room temperature and then warmed to 90° C. for 15 hours. A sample was withdrawn and quenched with an aqueous sodium citrate solution (1 M). The resulting aqueous solution was extracted with ethyl acetate. GC analysis of the organic phase showed the presence of 4-methyl-1,1'-biphenyl (1.466 mmol, 66% yield) and phenyltrimethylsilyl ether (0.264 mmol) and bitoluene (0.462 mmol) in the reaction mixture.

Comparative Example 9

Preparation of 2-phenyl pyridine by nickel catalyzed coupling of 2-methoxypyridine with p-tolylmagnesium bromide using $NiCl_2(PCy_3)_2$/2 $PCy_3$ in THF.

In a reaction flask was placed $NiCl_2(PCy_3)_2$ (58.5 mg, 0.0847 mmol), tridecane (345 mg, 1.875 mmol, as an internal standard), and 2-methoxypyridine (343 mg, 3.146 mmol). The Grignard reagent (1 M in THF, 6.2 mmol) was added to the above catalyst mixture under a nitrogen atmosphere at 0° C. The resulting solution was stirred for several minutes and warmed to room temperature for 15 hours. The reaction mixture was quenched with an aqueous sodium citrate solution (1 M). The resulting aqueous solution was extracted with MTBE (4×25 mL). The combined organic layer was washed with an aqueous HCl solution (2.5 M, 4×15 mL). The aqueous layer was then extracted with MTBE (1×25 mL). This solution was cooled to 0° C. and a dilute aqueous KOH solution was added until pH 8. The aqueous layer was extracted with MTBE (4×25 mL) and dried over $MgSO_4$. The resulting solution was filtered and concentrated under vacuum. The resulting residue was purified by silica gel chromatography (eluted with MTBE) to afford 2-phenylpyridine (368 mg, 75% yield).

In a separate experiment using the conditions described above with the exception that no nickel catalyst was added resulted in no observable reaction. Analysis of the crude reaction mixture by GC showed presence of 2-methoxypyridine with no significant amount, if any, of 2-phenylpyridine.

Comparative Example 10

Preparation of 4-methyl-1,1':2',1''-terphenyl by nickel catalyzed coupling of 2-methoxybiphenyl with p-tolylmagnesium bromide using $NiCl_2(PCy_3)_2$/2 $PCy_3$ in t-AmOMe.

In a reaction flask was placed $NiCl_2(PCy_3)_2$ (51.5 mg, 0.0746 mmol), $PCy_3$ (44.4 mg, 0.0.1586 mmol), tridecane (195.7 mg, 1.0613 mmol, as an internal standard), and 2-methoxybiphenyl (247.3 mg, 1.344 mmol). The solvent in the Grignard reagent (1 M in ether, 4.0 mmol) was exchanged with t-AmOMe (6.0 mL) and this solution was added to the above catalyst mixture under a nitrogen atmosphere at room temperature. The resulting solution was stirred for several minutes at room temperature and then warmed to 60° C. for 1 hour, 75° C. for 1.5 h and then 100° C. for 15 h. A sample was withdrawn and quenched with an aqueous sodium citrate solution (1 M). The resulting aqueous layer was extracted with ethyl acetate. GC analysis of the organic phase showed the presence 4-methyl-1,1':2',1''- terphenyl (1.186 mmol, 88% yield) and 2-methoxybiphenyl (0.100 mmol) and bitoluene (0.431 mmol) in the reaction mixture.

Comparative Example 11

Preparation of 6-(4-methylphenyl)-1,2,3,4-tetrahydronaphthalene by nickel catalyzed coupling of 6-methoxy-1,2,3,4-tetrahydronaphthalene with p-tolylmagnesium bromide using $NiCl_2$(dcpb)/dcpb in t-AmOMe. [dcpb=1,4-bis(dicyclohexylphosphino) butane]

In a reaction flask was placed $NiCl_2$(dcpb) (38.0 mg, 0.0655 mmol), dcpb (34.6 mg, 0.0768 mmol), tridecane (164.5 mg, 0.892 mmol, as an internal standard), and 6-methoxy-1,2,3,4-tetrahydronaphthalene (169.3 mg, 1.044 mmol). The solvent in the Grignard reagent (1 M in ether, 3.0 mmol) was exchanged with t-AmOMe (5.0 mL) and this solution added to the above catalyst mixture under a nitrogen atmosphere at room temperature. The resulting solution was stirred for several minutes at room temperature and then warmed to 80° C. for 15 hours. A sample was withdrawn and quenched into saturated aqueous ammonium chloride and was extracted with ethyl acetate. GC analysis of the organic phase showed the presence of 6-(4-methylphenyl)-1,2,3,4-tetrahydronaphthalene (0.363 mmol, 35% yield), bitoluene (0.216 mmol), and 6-methoxy-1,2,3,4-tetrahydronaphthalene (0.429 mmol) in the reaction mixture.

Comparative Example 12

Preparation of 6-(4-methylphenyl)-1,2,3,4-tetrahydronaphthalene by nickel catalyzed coupling of 6-methoxy-1,2,3,4-tetrahydronaphthalene with p-tolylmagnesium bromide using an in situ generated nickel catalyst (Niacac)$_2$/dcpp in THF. [dcpp=1,3-bis(dicyclohexylphosphino) propane]

In a flask was combined Ni(acac)$_2$ (48.0 mg, 0.182 mmol), dcpp (79.5 mg, 0.182 mmol), tridecane (235 mg, 1.275 mmol, as an internal standard), and 6-methoxy-1,2,3,4-tetrahydronaphthalene (592 mg, 3.64 mmol). The Grignard reagent (1 M in THF, 11.0 mmol) was added to this mixture under a nitrogen atmosphere at 0° C. The resulting solution was warmed to 60° C. for 15 hours. A sample was withdrawn and quenched into 1 M aqueous sodium citrate and was extracted with ethyl acetate. GC analysis of the organic phase showed the presence of 6-(4-methylphenyl)-1,2,3,4-tetrahydronaphthalene (0.397 mmol, 11% yield), bitoluene (0.602 mmol), and 6-methoxy-1,2,3,4-tetrahydronaphthalene (2.54 mmol) in the reaction mixture.

In addition, an experiment using 1,2-bis(dicyclohexylphosphino)ethane (dcpe) was also run under the conditions illustrated above. This GC analysis of this reaction showed the presence of 6-(4-methylphenyl)-1,2,3,4-tetrahydronaphthalene (2% yield) and 6-methoxy-1,2,3,4-tetrahydronaphthalene (77%).

It is understood that the examples and embodiments described herein are for illustrative purposes only and that various modifications or changes in light thereof will be suggested to persons skilled in the art and are to be included within the spirit and purview of this application and scope of the appended claims. All publications, patents and patent applications cited herein are hereby incorporated by reference in their entirety for all purposes.

What is claimed is:

1. A method for coupling an organomagnesium compound of the formula: $R^1MgX^1$ with an aromatic ether compound of the formula: $Ar^1$—$OR^2$ to produce a coupled aromatic compound of the formula: $Ar^1$—$R^1$, said method comprising admixing the organomagnesium compound with the aromatic ether compound in the presence of a nickel catalyst comprising a phosphino-ligand of the formula $PR^3R^4R^5$, wherein $R^1$ is selected from the group consisting of aryl and heteroaryl;

$R^2$ is selected from the group consisting of alkyl, heteroalkyl, cycloalkyl, aryl, aralkyl and a moiety of the formula —$SiR^9R^{10}R^{11}$, wherein each of $R^9$, $R^{10}$ and $R^{11}$ is independently a hydrocarbon moiety;

$Ar^1$ is aryl or heteroaryl;

$X^1$ is a magnesium metal ligand;

each of $R^3$ and $R^4$ is independently a saturated hydrocarbon moiety having from one to about twelve carbon atoms; and $R^5$ is selected from the group consisting of a saturated hydrocarbon moiety having from one to about twelve carbon atoms and an aryl moiety having from six to fourteen carbon ring atoms.

2. The method of claim 1, wherein the saturated hydrocarbon moiety is selected from the group consisting of $C_1$–$C_{12}$ alkyl and $C_3$–$C_{10}$ cycloalkyl.

3. The method of claim 2, wherein each of $R^3$ and $R^4$ is independently selected from the group consisting of isopropyl, methyl, tert-butyl, iso-butyl, neopentyl and cyclohexyl.

4. The method of claim 3, wherein $R^5$ is selected from the group consisting of isopropyl, methyl, tert-butyl, iso-butyl, neopentyl, cyclohexyl and phenyl.

5. The method of claim 4, wherein each of the phosphino-ligand is independently selected from the group consisting of triisopropylphosphine, dicyclohexylphenylphosphine, di-tert-butylmethylphosphine, triisobutylphosphine, tri-neopenylphosphine and tricyclohexylphosphine.

6. The method of claim 1, wherein $Ar^1$ is aryl.

7. The method of claim 6, wherein $Ar^1$ is optionally substituted phenyl.

8. The method of claim 7, wherein $R^2$ is methyl or ethyl.

9. The method of claim 8, wherein $R^1$ is aryl.

10. The method of claim 9, wherein $R^1$ is optionally substituted phenyl.

11. The method of claim 1, wherein the admixture further comprises at least about 2 equivalents of phosphine compound relative to the amount of the nickel catalyst, wherein the phosphine compound is of the formula: $PR^3R^4R^5$, wherein $R^3$, $R^4$ and $R^5$ are as defined in claim 1.

12. The method of claim 1 further comprising admixing the organomagnesium compound with the aromatic ether compound in a non-aromatic reaction solvent.

13. A process for producing a substituted aromatic compound of the formula:

$Ar^1$—$R^1$ said process comprising admixing an organomagnesium compound of the formula: $R^1MgX^1$ and an aromatic ether compound of the formula: $Ar^1$—$OR^2$ in a non-aromatic solvent in the presence of a nickel catalyst comprising a phosphino-ligand to produce the substituted aromatic compound, wherein $R^1$ is selected from the group consisting of aryl and heteroaryl;

$R^2$ is selected from the group consisting of alkyl, heteroalkyl, cycloalkyl, aryl, aralkyl and a moiety of the formula —$SiR^9R^{10}R^{11}$, wherein each of $R^9$, $R^{10}$ and $R^{11}$ is independently a hydrocarbon moiety;

Ar¹ is aryl or heteroaryl; and

X¹ is a magnesium metal ligand.

14. The process of claim 13, wherein the phosphino-ligand comprises a plurality of saturated hydrocarbons.

15. The process of claim 14, wherein the phosphino-ligand is of the formula:

$$PR^3R^4R^5,$$

wherein each of $R^3$ and $R^4$ is independently a saturated hydrocarbon moiety having from one to about twelve carbon atoms; and $R^5$ is selected from the group consisting of a saturated hydrocarbon moiety having from one to about twelve carbon atoms and an aryl moiety having from six to fourteen carbon ring atoms.

16. The process of claim 14, wherein each saturated hydrocarbon is independently selected from the group consisting of $C_1$–$C_{12}$ alkyl and $C_3$–$C_{10}$ cycloalkyl.

17. The method of claim 13, wherein the non-aromatic solvent is selected from the group consisting of THF, DME, 1,4-dioxane, THP, MTBE, diethyl ether, dicyclohexyl methyl amine, t-AmOMe, diisopropyl ether, DEM, di-n-butyl ether, and a combination of two or more solvents thereof.

18. The method of claim 17, wherein the non-aromatic solvent is selected from the group consisting of t-AmOMe, diisopropyl ether, DEM, di-n-butyl ether, and a combination of two or more solvents thereof.

* * * * *